United States Patent [19]

Dufau

[11] 4,378,280
[45] Mar. 29, 1983

[54] FIXED SLEEVE JUNCTION REFERENCE ELECTRODE

[75] Inventor: Oscar R. Dufau, Fullerton, Calif.
[73] Assignee: Graphic Controls Corporation, Buffalo, N.Y.
[21] Appl. No.: 353,342
[22] Filed: Mar. 1, 1982
[51] Int. Cl.³ .......................................... G01N 27/30
[52] U.S. Cl. ................................................. 204/195 F
[58] Field of Search ........................... 204/195 F, 1 H; 324/438

[56] References Cited

U.S. PATENT DOCUMENTS

| | | | |
|---|---|---|---|
| 3,298,944 | 1/1967 | Luck | 204/195 F |
| 3,790,463 | 2/1974 | Gealt | 204/195 F |

Primary Examiner—G. L. Kaplan
Attorney, Agent, or Firm—Michael G. Berkman

[57] ABSTRACT

In an electrode of the type having a reservoir for containing a reference electrolyte solution and a liquid junction for effecting electrical communication between said reference electrolyte solution and a sample solution, and including a seat and plug valve assembly of the electrode in communication with the reservoir and a sample solution, an improvement characterized in that a resiliently stressed spring contained within the reservoir biases the plug axially into mating engagement with the valve seat, and in that, upon application of displacement pressure axially against the plug, the latter automatically twists, axially, to execute a partial turn so that a valve-closing face of the plug laps or wipes against the seat and concurrently moves from engagement with the valve seat to open the valve assembly for fluid flow and cleansing flushing therethrough.

15 Claims, 3 Drawing Figures

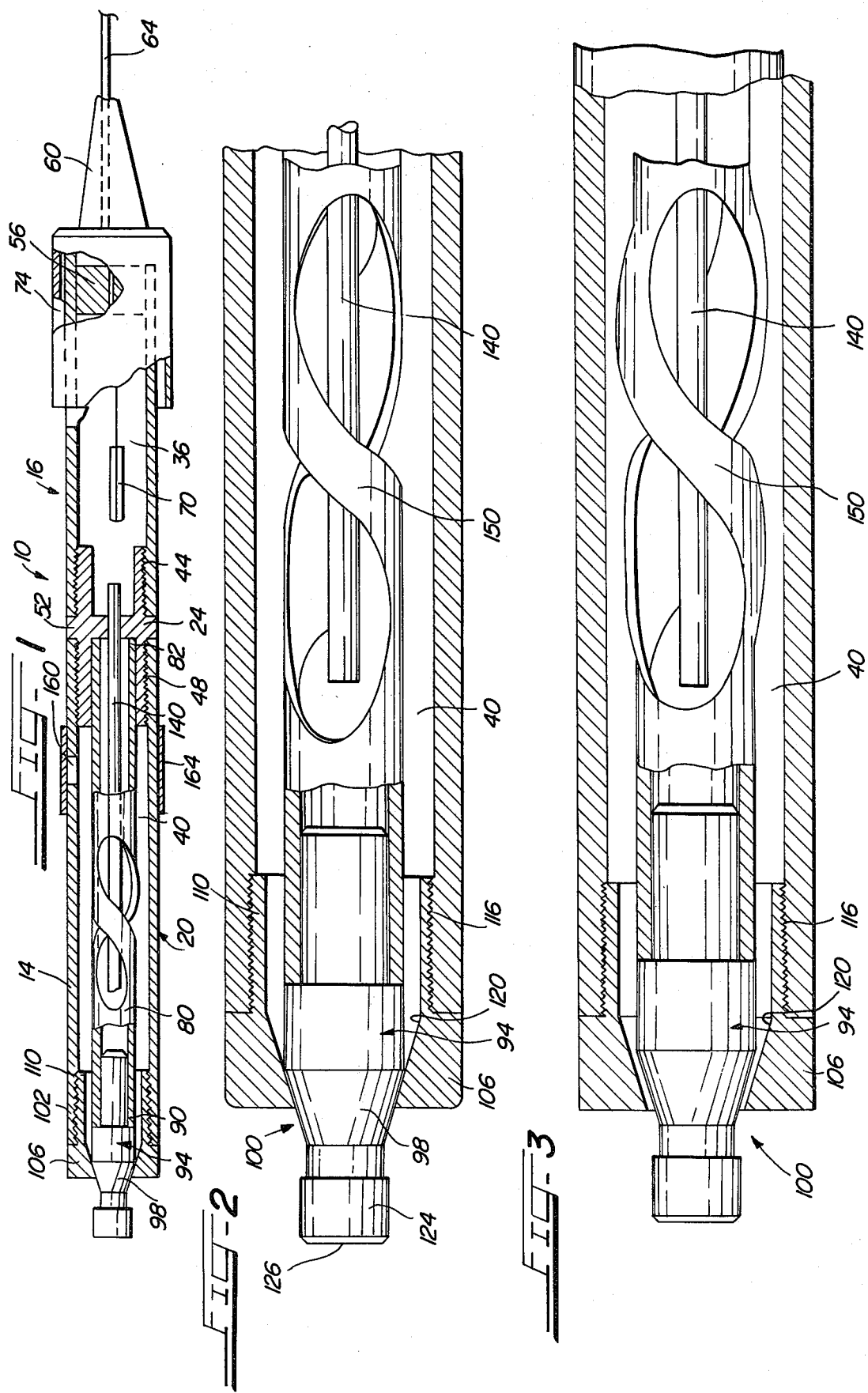

FIXED SLEEVE JUNCTION REFERENCE ELECTRODE

BACKGROUND OF THE INVENTION

The present invention relates generally to an electrode of the electrochemical type and useful as a reference electrode. More particularly, the present invention is directed to a fixed sleeve junction reference electrode finding utility in the measurement of the potential of solutions and for the determination of the concentration of specific ions in solution.

The scientific field in which the present invention lies is a complex one, and there are extensive scientific articles and treatises dealing with both the theory of operation and the methods of designing and constructing such electrodes. Specific publications have dealt with problems experienced in engineering electrodes of the general type involved in the subject invention, and there have been various proposals of methods for solving some of the problems recognized.

It is a general structural feature of electrodes of the type in which the present invention finds utility that an electrical connection between a salt solution contained in the electrode and a sample or test solution exterior of the electrode is made through a liquid junction or contact by means of a suitable duct of fluid conduit means formed in the physical configuration of the electrode itself.

In many chemical and electrochemical electrode determinations, it has been found necessary to wash or flush the liquid junction of the reference electrode to remove interfering sludge or slurry material or viscous matter derived from or contained in the test solution or test sample under investigation. In some type of reference electrodes, pourous plugs are used as the means for establishing the requisite liquid junction. Such plugs are conventionally cleaned by emersion in boiling salt solutions. In other types of electrodes the liquid junction is effected through a contact interface in which the abutting surfaces are somewhat roughened to permit limited transmittal of bridging solution between the interior of the electrode and the test solution. In the latter type of structure, described generally as a "sleeve-type" liquid junction, cleansing is achieved by physically separating the abutting surfaces and flushing solution between the displaced surfaces. Experience has shown that there is difficulty in separating the abutting surfaces without causing breakage of the assembly. In other instances, it has been found difficult to establish reliable flow-limiting interengagement of the abutting surfaces.

While extensive research has been conducted to develop electrode configurations and structures obviating the above and other difficulties experienced, no completely satisfactory sleeve-type junction reference electrode has heretofore been devised. It is, accordingly, a principal aim of the present invention to provide an improved liquid junction electrode which avoids the shortcomings of prior structures and ensures effective cleansing using simple procedures such as flushing.

SUMMARY OF THE INVENTION

It is a principal object of the present invention to provide an electrode having a wiping and flushing self-cleaning sleeve junction.

In a preferred embodiment of the invention, the desired wiping or lapping action is achieved by providing means for establishing relative rotation between mating components of a valve assembly including an interface through which the electrolyte salt solution of the electrode may diffuse to effect electrical communication with the test solution.

A related feature of the invention is that mating physical elements of the liquid junction valve assembly of the invention shift rotatively relative to one another and, simultaneously, retract from one another. The compound action ensures that the contacting surfaces are mechanically lapped and then separate to permit cleansing solution to flush between the facing surfaces.

Yet another important feature of the invention is that the valve assembly of the electrode includes a valve plug which is resiliently biased axially to bear against and functionally to abut the cooperating mating valve seat.

A related feature of the invention is that the spring mechanism acting upon the valve assembly functions as well to maintain the component elements in intersealing alignment and to provide the means by which the valve plug is rotated with respect to the valve seat in response to axial pressure applied to the valve plug.

In a preferred embodiment of the invention, the spring means is of an inert, non-metallic composition, obviating ion interference problems.

Still another important feature of the electrode of the invention is that the valve assembly is conveniently and simply resiliently opened upon merely impressing axial force against the end of a protruding valve plug.

A related advantage of the invention is that the degree to which the sleeve valve is open is readily and simply controlled by means of regulating the pressure applied and, accordingly, the extent to which the plug is physically displaced from the valve seat.

Yet another important functional feature ensuring the effective operation of the improved sleeve valve of the invention is that the mating parts are resiliently stressed and brought together in a manner which ensures proper alignment.

Still another important advantage of the sleeve valve of the invention is that the area of interfacial engagement or of contact between the plug and the cooperating seat is maintained essentially constant thereby ensuring precision and reproduceability of measurements carried out using the electrode of the invention.

It is another feature of the invention that rotation of the plug with respect to the mating seat occurs both during opening and closing of the valve to effect a wiping of the seat and valve faces in both a clockwise and counterclockwise direction.

An important mechanical feature of the electrode of the invention is that the spring mechanism for biasing the plug against the valve seat and for responding to axial pressure to open the valve assembly is fabricated from a tubular plastic element which has been cut to define lineally extending convolutes or flexible bands, the bands being resiliently deformable in response to axial pressure impressed against the end of the valve plug.

A related feature of the invention is that the application of axial pressure to the end of the plug establishes a rotational force vector in the elongated bands themselves, causing the plug to shift rotatively as it is displaced from the cooperating seat.

An important practical feature of the improved electrode of the invention is that it is readily manipulable using one hand, to open the end valve.

Yet another feature of the electrode of the invention is that the valve assembly is responsive to pressure applied against the plug rotatably to wipe against the seat of the valve and simultaneously to retract from the seat, and that upon release of applied pressure, the plug approaches toward and wipes or laps the seat and closes the valve.

While the electrode itself includes multiple chambers, it is a feature of the improved valve assembly of the invention that all moving parts involved are contained in a single electrode chamber. Thus, the possibility of contamination between chambers is markedly reduced.

Other and further objects, advantages, and features of the invention will become apparent from a consideration of the specifications in conjunction with the drawings.

DESCRIPTION OF THE DRAWING

FIG. 1 is a longitudinal sectional view of a preferred form of a reference electrode according to the invention, showing the arrangement of component elements thereof;

FIG. 2 is an enlarged fragmentary longitudinal sectional view of the electrode of FIG. 1 showing the end valve of the electrode in a closed position with the valve plug resiliently stressed in sealing engagement with the mating valve seat; and FIG. 3 is a view similar to that shown in FIG. 2 but depicting, schematically, the plug of the end valve displaced inwardly and spaced from the valve seat to define an open position of the end valve of the electrode.

DESCRIPTION OF THE PREFERRED EMBODIMENT

The aims and objects of the invention are achieved by providing in the reference electrode of the invention an end closure or valve assembly, including a valve plug and cooperating valve seat, so structurally engineered as to respond to axial pressure impressed against an end of the plug to effect, simultaneously, an opening of the valve as well as a rotational wiping of the plug face against the cooperating valve seat. The arrangement described facilitates a flushing, cleansing of the valve interface which constitutes the liquid junction structure of the electrode. In the specific arrangement described, the components are preferably fabricated of a non-corrosive material such as plastic, so as to deter attack of the valve surfaces through contact with the electrolyte solutions. The valve plug is biased into resiliently stressed engagement against the valve seat by means of a convoluted spring which is preferably also fabricated from plastic and constitutes a cutaway tubular element.

Referring now to the drawing, and particularly to FIG. 1, there is shown, for illustrative purposes and not in any limiting sense, a preferred embodiment of a fixed sleeve junction reference electrode 10 according to the invention. The electrode 10 constitutes an elongated tubular body or shell 14, generally cylindrical in form and including an upper cylinder 16 and a coaxially-in-line lower cylinder 20. The two cylindrical sections 16 and 20 are joined to one another by means of an internal coupling, sleeve or bushing 24 which includes an integrally formed transverse wall dividing the electrode body into separate upper and lower chambers 36 and 40. For ease of assembly and disassembly, the tubular sections 16 and 20 are fastened to the cylindrical coupling 24 by means of cooperating threads 44 and 48. In the specific embodiment of the electrode shown, the internal coupling 24 includes a radially outwardly extending annular ring 52 against which the ends of the tubular sections 16 and 20 abut.

As illustrated in FIG. 1, the upper chamber 36 is sealed near its end by means of an internal plug 56. The primary end seal 56 is augmented by a secondary sealing assembly 60 which extends beyond the cylindrical body of the electrode and tapers downwardly to define a generally conical structure. Sealed in and extending through the primary seal 56 and the secondary seal 60 and generally coaxial with the electrode itself is a conductive element in the form of a wire 64, the latter being attached to and in electrical communication with one half cell element 70 in the upper chamber 36. An open-ended sleeve-like cap through which the secondary seal assembly 60 projects, is slidably fastened to envelope the end of the upper chamber, as indicated schematically in FIG. 1.

Extending coaxially within the lower chamber 40 and spaced from the cylindrical walls 14 of the electrode is an elongated hollow tube 80 the upper end 82 of which is slidably received within and frictionally held in the tub coupler or joinder 24, the end 82 of the tube 80 bottoming against the transverse wall of the coupling element 24. Inserted into to extend from the opposite end 90 of the tube 80 is a plug 94 having a rearwardly tapering frusto conical section 98. The plug 94 is one component of the improved valve assembly 100 of the invention.

Inserted into and secured within the end 102 of the body 14 adjacent the plug 94 is an annular cap 106 integrally formed with an annular skirt 110 which extends interiorly of and in contact with the end portion 102 of the electrode body 14. Preferably, the skirt and the embracing tubular sleeve 102 are coupled by means of cooperating threads 116.

The annular cap 106 is provided with a through axial opening having a bounding surface 120 which defines a frusto conical surface having an annular configuration corresponding essentially to the frusto conical surface 98 of the plug 94 for mating therewith.

As shown in FIG. 2, the maximum diameter of the conical section 98 exceeds the minimum diametric dimension of the opening of the cap 106 so that the conical surface 98 abuts contiguously the cooperating surface 120 of the sleeve 106, the latter serving as a seat for the plug 94. Also as shown in the drawings, the plug 94 terminates at its outwardly extending end in a generally cylindrical stub rod portion 124 having a substantially flat end surface 126 for application of finger pressure thereto.

As best seen in FIG. 1, electrical communication between the interior of the upper chamber 36 and the lower chamber 40 is achieved by means of a porous rod 140 which is sealed in to extend through the tube coupler 24. The rod 140 extends generally coaxially within the electrode itself.

As indicated clearly in FIG. 2, the overall length dimension of the internal tube 80, and including the end plug 94 are such that, upon attachment of the end cap or sleeve 106 to the valve body 102, the internal conical surface 120 of the sleeve 106 it is brought stressingly to bear against the cooperating valve surface 98 of the plug 94.

Also as clearly shown, the body of the internal tube 80 is cutaway in a zone intermediate its ends to define a plurality of convolute ribbons or bands 150. The latter function as spring elements permitting the plug end 94 of the assembly to be urged axially inwardly of the embracing sleeve-like cap 106 to establish a stressed and abutting seating engagement between the cooperating surfaces 98 and 120 of the plug 94 and the annular seat 106, respectively.

The "compressability" axially of the spring bands 150 functions as well to permit axially inwardly displacement of the plug 94 to effect a spatial separation between the surfaces 120 and 98 of the cooperating sleeve valve elements 106 and 94 upon impressing axial pressure inwardly on the plug end 126. In this manner there is established a spatial configuration such as indicated schematically in FIG. 3, which depicts the valve assembly 100 in an "open" position.

It will also be appreciated, based upon the foregoing description and recognizing the convoluted form of the spring bands 150, that upon exertion of axially inwardly directed pressure against the end 126 of the valve plug 124, the plug moves not only axially inwardly but executes a rotational displacement to effect a wiping or lapping action between the abutting conical valve surfaces 98 and 120 of the plug 94 and the annular seat 106, respectively.

As shown in FIG. 1, the tubular wall 14 of the lower compartment 40 is provided with a port 160 by means of which the lower chamber 40 is filled with fluid and by which refilling operations may be conducted. The same port 160 is useful as a means for introducing liquid when the valve assembly 100 is open and it is desired to "flush out" the chamber 40 itself. A sleeve 164 is relied upon to close the port 160 during periods of nonuse. The sleeve 164 is slidable linearly along the tubular wall 14 to expose the port 160, as required.

It will also be appreciated based upon the foregoing detailed description that the convoluted spring or torsion ribbons 150 act to impart a rotational action to the plug 94 as the latter is urged axially inwardly into the electrode assembly, to effect a wiping or lapping action of the valve surfaces 98 and 120 in a given annular mode. The ribbons 150 serve as well to impart as to cause a lapping engagement between the abutting surfaces 98 of the plug and 120 of the sleeve when one releases the impressed axial pressure to permit the plug 94 to shift axially outwardly of the electrode assembly. Thus, the improved valve of the present electrode ensures wiping action in each of two opposed modes, to minimize any possibility of build-up of interfering sludge or debris at the valve interfaces.

The improved valve assembly of the invention renders it practical to control the degree to which the valve is opened by controlling the extent to which the plug 94 is displaced axially inwardly into the cavity 40.

While preferred embodiments of the invention have been illustrated and described, other variations may be made utilizing the inventive concepts herein disclosed. It is intended that all such variations in functional structures be considered as within the scope of the invention as defined in the following claims.

What is claimed is:

1. In an electrode including a tubular housing defining a longitudinally extending bounding wall of a chamber for retaining a fluid therewithin, first end closure means at a first end of said housing for restricting fluid flow from said chamber at said first end thereof, second end closure means for controlling fluid flow from a second end of said chamber displaced axially from said first end thereof;

the improvement wherein said second end closure means comprises valve means including annular valve seat means and cooperating valve plug means for fluid-tight mating interengagement, said improvement further comprising spring means biasing said plug means into fluid-retentive, fluid-flow-restricting engagement with said valve seat means, said spring means being responsive to pressure applied to said plug means axially thereof and inwardly of said chamber forcibly to dislodge said valve plug means from said valve seat means thereby to open said valve means.

2. The improvement as set forth in claim 1 wherein said spring means is responsive to pressure applied axially through said plug means and inwardly of said chamber to effect tensioned axial rotation of said plug means during dislodgement thereof from said seat means.

3. The improvement as set forth in claim 2 wherein activation of said spring means through application of pressure to said plug means develops torsional rotational forces acting on said plug means.

4. The improvement as set forth in claim 1 wherein said spring means comprise flexible band means within said chamber and extending lineally in a zone intermediate said plug means and said first end of said tubular housing, and further comprising means coupling said plug means to said band means for transmittal of band-means-deforming force thereto upon application of mechanical pressure axially to said plug means, said band means being resiliently distortable in response to pressure applied axially thereto to establish a rotational force vector in said band means, thereby to shift said plug means through an annular rotational increment upon forced dislodgement of said plug means axially from said valve seat means.

5. The structure as set forth in claim 4 wherein said band means are continually in a tensioned state and wherein tension forces exerted by said band means serve to bias said plug means of said valve means into resilient mating abutment against said seat means of said valve means.

6. The improvement as set forth in claim 1 wherein said spring means comprises thin-walled tube means within and generally coaxial with said housing, said tube means including lineally extending wall means bridging between said plug means and said first end of said chamber, said tube means being formed with elongated slot means extending through said wall means thereof to define resiliently distortable rib-like segments of said wall means essentially coextensive with said slot means, said rib-like segments being responsive to axial pressure transmitted therealong through said plug means forcibly to distort said segments and to store contortional energy therewithin, whereby upon removal of compressive axial-pressure therealong said segments revert to an original elongate configuration and simultaneously urge said plug means to seat in said valve seat means.

7. The improvement as set forth in claim 6 wherein said slot means are generally tortuous in form.

8. The improvement as set forth in claim 6 wherein said rib-like segments are generally convolute.

9. The improvement as set forth in claim 6 wherein said rib-like segments include at least two such segments.

10. The improvement as set forth in claim 1 wherein said electrode is readily manipulable using one hand, said electrode being adapted for one-hand gripping and, through the arrangement and disposition of structural components set forth in claim 1, for simultaneous application of finger pressure to said plug means to open said valve means while using the same hand employed in the gripping of said electrode.

11. The improvement as set forth in claim 1 wherein application of pressure axially to said plug means develops simultaneous torsional rotational forces impressed upon said plug means and effects rotation of said plug means with respect to said seat means during opening and during closure of said valve means to provide a lapping, wiping action at said seat means during flushing of said valve means.

12. The improvement as set forth in claim 10 wherein rotation of said plug means is in one direction during opening of said valve means and is in an opposite direction during closure of said valve means to effect lapping of said plug means against said seat means in two opposed rotational modes.

13. The improvement as set forth in claim 1 and characterized in that said valve seat means and said valve plug means comprise non-metallic compositions.

14. The improvement as set forth in claim 1 wherein said plug means and said seat means of said valve means include mating surfaces which are generally truncated cones as viewed in traverse longitudinal section.

15. The improvement as set forth in claim 14 wherein said plug means of said valve means is responsive to pressure applied axially thereagainst to shift said plug means from fluid sealing abutment against said valve seat means to provide annular fluid flow passage means between said plug means and said seat means, said passage means defining an annular port having a transverse cross-sectional area varying with and being a function of a degree of displacement of said plug means from said seat means thereby providing selectively variable fluid flow rates through said valve means, said variable fluid flow rates being correlated with said degree of displacement of said plug means from said seat means.

* * * * *